United States Patent
De Man et al.

(10) Patent No.: US 10,736,594 B2
(45) Date of Patent: Aug. 11, 2020

(54) DATA-BASED SCAN GATING

(71) Applicant: General Electric Company, Schenectady, NY (US)

(72) Inventors: Bruno Kristiaan Bernard De Man, Clifton Park, NY (US); Eri Haneda, Clifton Park, NY (US); Jed Douglas Pack, Glenville, NY (US); Bernhard Erich Hermann Claus, Niskayuna, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 74 days.

(21) Appl. No.: 16/200,175

(22) Filed: Nov. 26, 2018

(65) Prior Publication Data
US 2020/0163639 A1    May 28, 2020

(51) Int. Cl.
*A61B 6/00*     (2006.01)
*G06T 7/20*     (2017.01)
*G06N 3/08*     (2006.01)

(52) U.S. Cl.
CPC .............. *A61B 6/5205* (2013.01); *A61B 6/54* (2013.01); *G06N 3/084* (2013.01); *G06T 7/20* (2013.01); *G06T 2207/10081* (2013.01); *G06T 2207/10088* (2013.01)

(58) Field of Classification Search
CPC ........ A61B 6/5205; A61B 6/54; G06N 3/084; G06T 7/20; G06T 2207/10081; G06T 2207/10088
See application file for complete search history.

(56) References Cited

U.S. PATENT DOCUMENTS

| 7,415,093 | B2 | 8/2008 | Tkaczyk et al. |
| 7,522,744 | B2 | 4/2009 | Bai et al. |
| 7,974,682 | B2 * | 7/2011 | Gonzalez Molezzi ............ A61B 6/481 600/413 |
| 7,983,460 | B2 | 7/2011 | Licato et al. |
| 9,269,166 | B2 | 2/2016 | Hansis et al. |
| 9,430,855 | B2 | 8/2016 | Kohara |

(Continued)

FOREIGN PATENT DOCUMENTS

WO     2008017493 A2    2/2008

OTHER PUBLICATIONS

Kachelriess, Mac, et al.; "Kymogram detection and kymogram-correlated image reconstruction from subsecond spiral computed tomography scans of the heart", Medical Physics, vol. 29, Issue: 7, pp. 1489-1503, Jul. 2002.

(Continued)

Primary Examiner — Mark R Gaworecki
(74) Attorney, Agent, or Firm — Fletcher Yoder, P.C.

(57) ABSTRACT

In accordance with the present disclosure, the present technique finds a diagnostic scan timing for a non-static object (e.g., a heart or other dynamic object undergoing motion) from raw scan data, as opposed to reconstructed image data. To find the scan timing, a monitoring scan of a patient's heart is performed. In the monitoring scan, the patient dose may be limited or minimized. As the projection data is acquired during such a monitoring scan, the projection data may be subjected to sinogram analysis in a concurrent or real-time manner to determine when to start (or trigger) the diagnostic scan.

20 Claims, 5 Drawing Sheets

(56) References Cited

U.S. PATENT DOCUMENTS 9,517,042 B2 12/2016 Hsieh et al.
2019/0231288 A1* 8/2019 Profio .................. A61B 6/42

OTHER PUBLICATIONS

Lu, Wei, et al.; "Reduction of motion bluffing artifacts using respiratory gated CT in sinogram space: A quantitative evaluation", The International Journal of Medical Physics Research and Practice, Oct. 17, 2005.

Ertel, Dirk, et al.; "Rawdata-based detection of the optimal reconstruction phase in ECG-gated cardiac image econstruction", Medical Image Computing and Computer Assisted Intervention Society, pp. 348-355, 2006.

Ertel, Dirk, et al.; "Validation of a raw data-based synchronization signal (kymogram) for phase-correlated cardiac mage reconstruction", European Radiology, vol. 18, Issue: 2, pp. 253-262, Feb. 2008.

Ertel, Dirk et al.; "Real-time determination of the optimal reconstruction phase to control ECG pulsing in spiral cardiac CT", Physica Medica, vol. 25, Issue:3, pp. 122-127, Sep. 2009.

* cited by examiner

DATA-BASED SCAN GATING

TECHNICAL FIELD

The subject matter disclosed herein relates to timing the acquisition of scan data, such as computed tomography scan data, based on real-time analysis of preliminary scan data.

BACKGROUND

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

In the case of cardiac scans, the motion associated with the heart and respiration may provide challenges to acquiring useful images. To help account for such motion, cardiac scans typically require the use of an electrocardiograph (ECG) device which measures electrical impulses traveling across the heart muscle to trigger contractions. The ECG can monitor cardiac phase within a cardiac cycle such as diastole and systole from the signal. Typically, least cardiac motion is observed in end-diastole and end-systole phases of the cardiac cycle.

In traditional cardiac CT scanning, the ECG signal is recorded during the CT scan acquisition to trigger the CT scan during a quiescent phase and minimize cardiac motion artifacts or to retrospectively select the time interval at which to center the reconstruction (relative to the entire scan duration over which data was collected). Typically, some "phase padding" is included, i.e. the scan duration is extended over some extra time window to make sure at least some portion of the scan happened at a quiescent phase. In ECG modulation the ECG signal is used to modulate the tube current, i.e., to increase it, during the desired cardiac phase. However, recording an ECG signal typically requires placing a multi-lead ECG apparatus, which is time-consuming and prone to errors.

For some CT applications such as CT angiography, a contrast agent (e.g. iodine) is injected through a vein to increase visibility of blood vessels and other organs. Use of analogous contrast enhancing agents may be employed in other imaging modalities as well, such as in the context of magnetic resonance imaging (MRI). Since it takes multiple seconds for the contrast bolus to arrive in the organs of interest and the bolus disappears again a few seconds later, it is important to time the CT scan appropriately so that images are acquired when the contrast agent concentration is at (or near) peak in the target region of interest (ROI) or vessel, or generally near the desired phase of the contrast uptake and/or washout process.

Traditionally, during a monitoring phase scanning at low dose and real-time image reconstruction is repeatedly performed to track the contrast bolus level of a target vessel (or appropriately selected nearby anatomy). Once the bolus level exceeds a threshold in the reconstructed image, the diagnostic CT scan starts. However, the extra scan and reconstruction steps are time consuming and need to be done repeatedly. Moreover, there is always some degree of delay between the preparatory or monitoring phase and the actual diagnostic phase, so the prediction of when the right level of opacification will occur may be inaccurate.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a method is provided for estimating an optimal scan timing for a diagnostic image acquisition scan of a non-static object. In accordance with this method, a monitoring scan is performed using scan parameters different than those used in the diagnostic image acquisition scan, wherein the monitoring scan generates unreconstructed scan data. An object motion phase of the non-static object is estimated as the monitoring scan is being performed based on the unreconstructed scan data. A diagnostic scan trigger is determined as the monitoring scan is being performed based on at least the object motion phase. The diagnostic image acquisition scan is performed based on the diagnostic scan trigger such that the diagnostic image acquisition occur in substantially real-time relative to the determination of the diagnostic scan trigger.

In a further embodiment, an imaging system is provided. In accordance with this embodiment, the imaging system comprises: a memory encoding processor-executable routines and a processing component configured to access the memory and execute the processor-executable routines. The routines, when executed by the processing component, cause the processing component to: perform a monitoring scan using scan parameters different than those used in a diagnostic image acquisition scan, wherein the monitoring scan generates unreconstructed scan data; estimate an object motion phase of a non-static object as the monitoring scan is being performed based on the unreconstructed scan data; determine a diagnostic scan trigger as the monitoring scan is being performed based on at least the object motion phase; and perform the diagnostic image acquisition scan based on the diagnostic scan trigger such that the diagnostic image acquisition occur in substantially real-time relative to the determination of the diagnostic scan trigger.

In an additional embodiment, a non-transitory machine-readable storage medium storing executable instructions is provided. In accordance with this embodiment, the instructions, when executed by a processor, cause operations to be performed comprising performing a monitoring scan using scan parameters different than those used in a diagnostic image acquisition scan, wherein the monitoring scan generates unreconstructed scan data; estimating an object motion phase of a non-static object as the monitoring scan is being performed based on the unreconstructed scan data; determining a diagnostic scan trigger as the monitoring scan is being performed based on at least the object motion phase; and performing the diagnostic image acquisition scan based on the diagnostic scan trigger such that the diagnostic image acquisition occur in substantially real-time relative to the determination of the diagnostic scan trigger.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
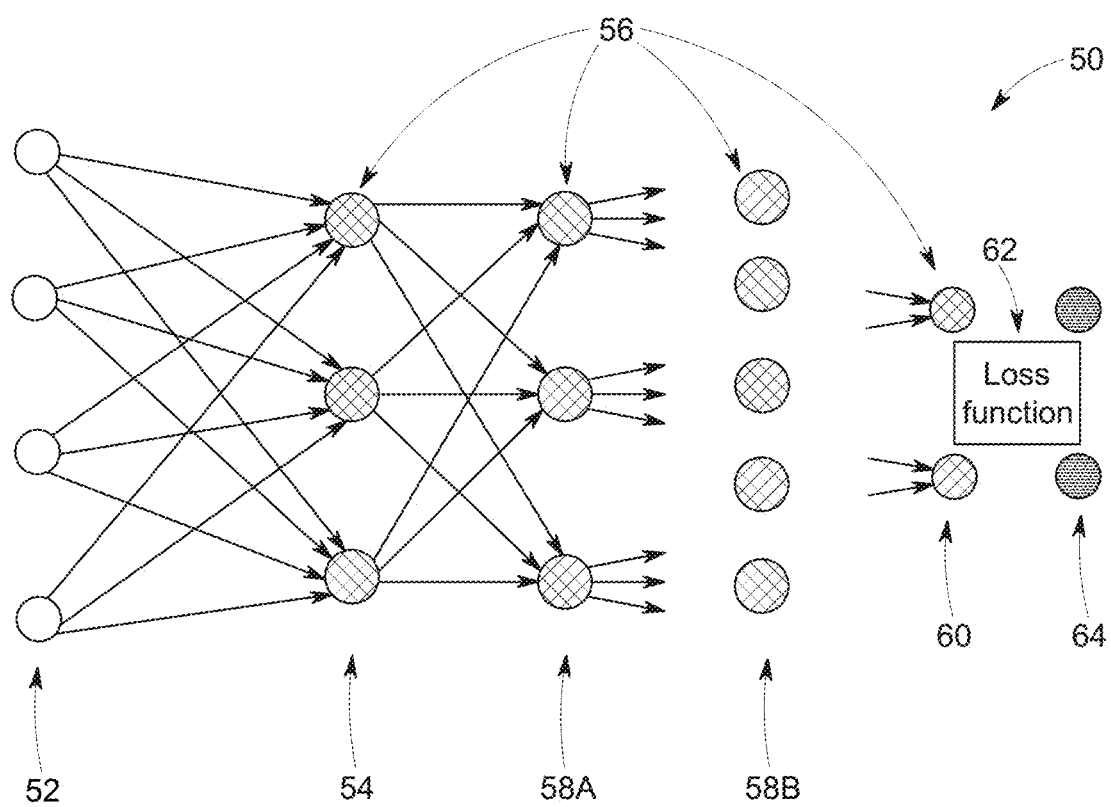
FIG. 1 depicts an example of an artificial neural network for training a deep learning model, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts where periods of reduced or otherwise favorable motion or lack of motion (or otherwise favorable imaging conditions, like peak opacification) occur in the imaged field of view, including industrial and/or security related non-destructive inspection. In general, the present disclosure may be useful in any imaging or screening context or image processing field where a set or type of acquired data acquired in the presence of periodic or nearly periodic motion undergoes a reconstruction process to generate an image or volume.

Furthermore, while the following discussion focuses on standard images or image volumes, it should be understood that the same approach can also be applied to sets of images or image volumes corresponding to different aspects of the scan. For example, spectral CT produces a set of images, including monochromatic images at different energies as well as basis material decomposition images. Or as another example, dynamic CT or PET produces a set of images at different time points. The current disclosure may be applied to these sets or types of images as well as others.

Though CT and computed tomography angiography (CTA) examples are primarily provided herein, it should be understood that the disclosed technique may be used in other imaging modality contexts where reconstruction processes are employed. For instance, the presently described approach may also be employed on data acquired by other types of tomographic scanners including, but not limited to, magnetic resonance imaging (MRI) scanners.

As discussed herein, scan timing of cardiac imaging, such as cardiac CT, is important because it directly impacts image quality due to heart motion, due to respiratory motion, and due to contrast bolus arrival time. To reduce motion-related issues, cardiac image scanning should be performed when cardiac motion is minimum. In conventional approaches, the cardiac motion is monitored by an electrocardiogram (ECG) device to find end-diastole or end-systole stage for each cardiac cycle. Then, the scan (e.g., a cardiac CT scan) is triggered such that the diagnostic scan data is acquired when the heart is in a phase with relatively little motion. Triggering, as used herein, may refer to switching the X-ray tube ON and transmitting X-rays or it may refer to increasing or adjusting one or more scan operating parameters (e.g., tube current, tube voltage, and so forth) so as to perform the acquisition of diagnostic image data. If contrast agent is injected to the patient, the scan timing may also be synchronized with the arrival time of the contrast agent to a target region or vessel. For instance, the scan may preferably be performed during the peak opacification in the target region.

Conventionally, there are two ways to predict contrast arrival time: 'timing bolus' and 'smart prep'. With a timing bolus, a small amount of contrast is injected to a patient in a pre-session and the patient is scanned repeatedly (with low dose) to find the time delay from injection to opacification of the region of interest (ROI). In 'smart prep', there is no separate session. The contrast agent is injected only once, in a monitoring phase repeated scanning (with low dose) of a specific region of interest is performed, and the contrast agent in a small region is monitored until it reaches a certain threshold. Within the "smart prep" case, a clinician may alternatively prefer to manually trigger the diagnostic scan based on a visual inspection of the series of smart prep images as they appear rather than relying on a quantitative threshold of the contrast within a predefined ROI (this may help mitigate fluctuations due to breathing and cardiac motion as well as the somewhat limited temporal sampling). In both the timing bolus and smart prep cases, the contrast agent opacification is evaluated in the reconstructed image domain, i.e., not in the raw acquisition data. The target slices are reconstructed repeatedly, then the voxel value of target ROI or vessel (or suitable nearby anatomy region) is evaluated (e.g., plotted) vs. time. From the time profile (i.e., the reconstructed voxel intensity in the ROI as a function of time), the time of predicted peak opacification is estimated. The scan may be also synchronized to patient's respiratory motion, such as based on signals from a patient-worn measurement device.

In contrast to such techniques, the present technique finds an optimal scan timing for a non-static object (e.g., a heart or other dynamic object undergoing motion in the second to sub-second time-frame) from raw scan data (e.g., projection data or sinogram data in the case of CT) as opposed to reconstructed image data (which is used in conventional approaches). The term "raw" data is only used herein to indicate that the data has not yet been backprojected (or reconstructed) to the image space. However, as used herein, in some embodiments "raw" data may still have undergone certain pre-reconstruction processing such as, but not limited to, gain correction, air scan normalization, bad-pixel correction, negative log, beam hardening correction, and so forth. To find an optimal scan timing from scan data, a scan of a patient's heart is performed at a low dose, which is referred to herein as a monitoring scan. In the monitoring scan, the patient dose may be limited or minimized because this is not a diagnostic scan (i.e., no diagnostic image will be generated from the raw scan data acquired during this monitoring phase). To minimize the dose, in one embodiment, the X-ray tube may be pulsed, resulting in a sparse-view dataset (sinogram), corresponding to lower radiation dose.

As the projection data is acquired during such a monitoring scan, the projection data may be subjected to sinogram analysis as it is acquired to determine when to start (or trigger) the diagnostic scan such that the diagnostic acquisition is controlled in a real-time or concurrent manner. As used herein, such real-time or concurrent diagnostic acquisition control may vary based on the context. For example, in a cardiac imaging context, such real-time acquisition control may allow triggering of the diagnostic acquisition within 1 second (e.g., within 0.75, 0.5, 0.25, or 0.1 seconds) of acquisition of the corresponding monitoring projection data. However, in the context of perfusion imaging real-time acquisition control may allow triggering of the diagnostic acquisition within 10 seconds (e.g., within 7.5, 5, 2.5, or 1 seconds) of acquisition of the corresponding monitoring projection data. Thus, as projection data from a monitoring scan is acquired, it may be analyzed, such as using a machine learning model as discussed herein, to evaluate whether or not to trigger a transition to the diagnostic scan (or when to trigger the transition to the diagnostic scan). If the answer is no (e.g., since the bolus contrast is not sufficiently high for diagnostic imaging, or the confidence in the current cardiac phase estimate is not very high), in some instances the monitoring scan will continue to acquire and analyze more projection data until such time as a projection data is acquired that meets the criteria to trigger diagnostic acquisition.

With this in mind, in one implementation, the present sinogram-based cardiac phase monitoring and bolus tracking technique is based solely on raw (i.e., un-reconstructed) CT scan data and thus can be performed without an ECG device or ECG signal. This can help reduce patient stress and operator burden. Further, the present technique eliminates the need for a separate timing bolus and associated scans and therefore saves time, contrast dose, and radiation dose. In smart prep contexts, there is a delay between the smart prep scanning (monitoring stage) and the actual diagnostic scan in which data to be reconstructed into a diagnostic image is acquired. This delay is made up of several parts, including the time to reconstruct the last smart prep image, the time it takes to open the pre-patient collimator, and the time it takes to move the table to the correct z position (i.e., position along the bore axis of the scanner. This delay is also reduced in the proposed technique, resulting in improved timing accuracy. The reduction of the delay is possible because there is no need for reconstruction, the pre-patient collimator will already be open, and the table can already be positioned at the position needed for the diagnostic scan during the monitoring scan. Additionally, the present technique can also eliminate the need for using a respiratory device for respiratory motion or phase estimation. The present technique thereby finds an optimal scanning time for the start or triggering of the diagnostic scan, such that image quality degradation (in the final reconstructed diagnostic image) due to cardiac motion, respiratory motion, non-optimal bolus contrast level and similar factors is minimized. The scan timing may be determined based on the estimated motion state (or motion phase) of the cardiac and/or respiratory motion, as well as the bolus contrast level (or other relevant bolus parameter) which are estimated based on the raw scan data acquired during the monitoring phase, according to one aspect of the present technique. According to another aspect, the scan timing is determined directly from the raw scan data collected during the monitoring phase.

With the preceding introductory comments in mind, some generalized information is provided both to indicate general context of the present disclosure and to facilitate understanding and explanation of certain of the technical concepts described herein.

As discussed in greater detail below, deep learning and similar approaches may be employed in certain contexts with respect to the present technique. For example, as discussed below, deep-learning approaches may be employed with sinogram analysis and corresponding motion phase and bolus parameter estimation, or estimation of optimal scan timing. In certain implementations, such deep-learning approaches may utilize neural networks in this analysis and estimation in furtherance of acquiring, processing, and reconstructing cardiac scan data used to generate tomographic images, such as CT, PET, SPECT, C-arm, phase-contrast, and MR images. Neural networks as discussed herein may encompass deep neural networks, fully connected networks, convolutional neural networks (CNNs), perceptrons, auto encoders, recurrent networks, wavelet filter banks based neural networks, or other machine learning models. These techniques are referred to herein as deep learning techniques, though this terminology may also be used specifically in reference to the use of deep neural networks, which is a neural network having a plurality of layers.

As discussed herein, deep learning techniques (which may also be known as deep machine learning, hierarchical learning, or deep structured learning) are a branch of machine learning techniques that employ mathematical representations of data and artificial neural networks for learning. By way of example, deep learning approaches may be characterized by their use of one or more algorithms to extract or model high level abstractions of a type of data of interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In a data processing or reconstruction context, this may be characterized as different layers corresponding to the different feature levels or resolution in the data.

In general, the processing from one representation space to the next-level representation space can be considered as one 'stage' of the process. Each stage of the neural processing can be performed by separate neural networks or by different parts of one larger neural network. For example, as discussed herein, one or more deep learning networks may be used to provide scan timing (or gating) of a diagnostic cardiac image acquisition process.

As discussed herein, as part of the initial training of deep learning processes to solve a particular problem, training data sets may be employed that have known input values (e.g., input images, projection data, emission data, magnetic resonance data, and so forth) and known or desired values for a final output associated with the input data (e.g., cardiac motion state or phase, respiratory motion state or phase, combined cardiac and respiratory motion state, start timing of diagnostic scan, and so forth) of the deep learning process. The training of a single stage may have known input values corresponding to one representation space and known output values corresponding to a next-level representation space. In this manner, the deep learning algorithms may utilize (either in a supervised or guided manner or in an unsupervised or unguided manner) the known or training data sets until the mathematical relationships between the input data and desired output(s) are discerned and/or the mathematical relationships between the inputs and outputs of each layer are discerned and characterized. Similarly, separate validation data sets may be employed in which both the input and desired target values are known, but only the input values are supplied to the trained deep learning algorithms, with the outputs then being compared to the outputs of the deep learning algorithm to validate the prior training and/or to prevent over-training/over-fitting.

With the preceding in mind, FIG. 1 schematically depicts an example of an artificial neural network 50 that may be trained as a deep learning model as discussed herein. In this example, the network 50 is multi-layered, with a training input 52 and multiple layers including an input layer 54, hidden layers 58A, 58B, and so forth, and an output layer 60 and the training target 64 present in the network 50. Though described as a separate, distinct layer, the input layer 54 may in certain contexts also be a hidden layer. Each layer, in this example, is composed of a plurality of "neurons" or nodes 56. The number of neurons 56 may be constant between layers or, as depicted, may vary from layer to layer. Neurons 56 at each layer generate respective outputs that serve as inputs to the neurons 56 of the next hierarchical layer. In practice, a weighted sum of the inputs with an added bias is computed to "excite" or "activate" each respective neuron of the layers according to a generally non-linear activation function, such as rectified linear unit (ReLU), sigmoid function, hyperbolic tangent function, or otherwise specified or programmed. The outputs of the final layer constitute the network output 60 (e.g., cardiac and/or respiratory motion state, bolus parameter, scan timing) which, in conjunction with the training target 64, are used to compute some loss or error function 62, which will be backpropagated to guide the network training. While FIG. 1 depicts a network consisting of fully connected layers, other models and elements for individual layers as well as for the larger network may be considered as well as mentioned herein above. For example, convolutional networks (CNNs), pooling layers, etc. may be used. Also, some outputs of certain layers may be connected to layers farther down in the processing chain. For example, a U-Net like architecture may be used, as well as other network architectures.

The loss or error function 62 measures the difference between the network output and the training target. In certain implementations, the loss function may be the mean squared error (MSE). Alternatively, the loss function 62 could be defined by other metrics associated with the particular task in question, such as a softmax function.

To facilitate explanation of the present motion state estimation approach (or scan timing, etc.) using deep learning techniques, the present disclosure primarily discusses these approaches in the context of a CT or C-arm system. However, it should be understood that the following discussion may also be applicable to other image modalities and systems including, but not limited to magnetic resonance imaging (MM), as well as to non-medical contexts or any context where motion estimation is employed to gate a scan acquisition process.

Figure 2:
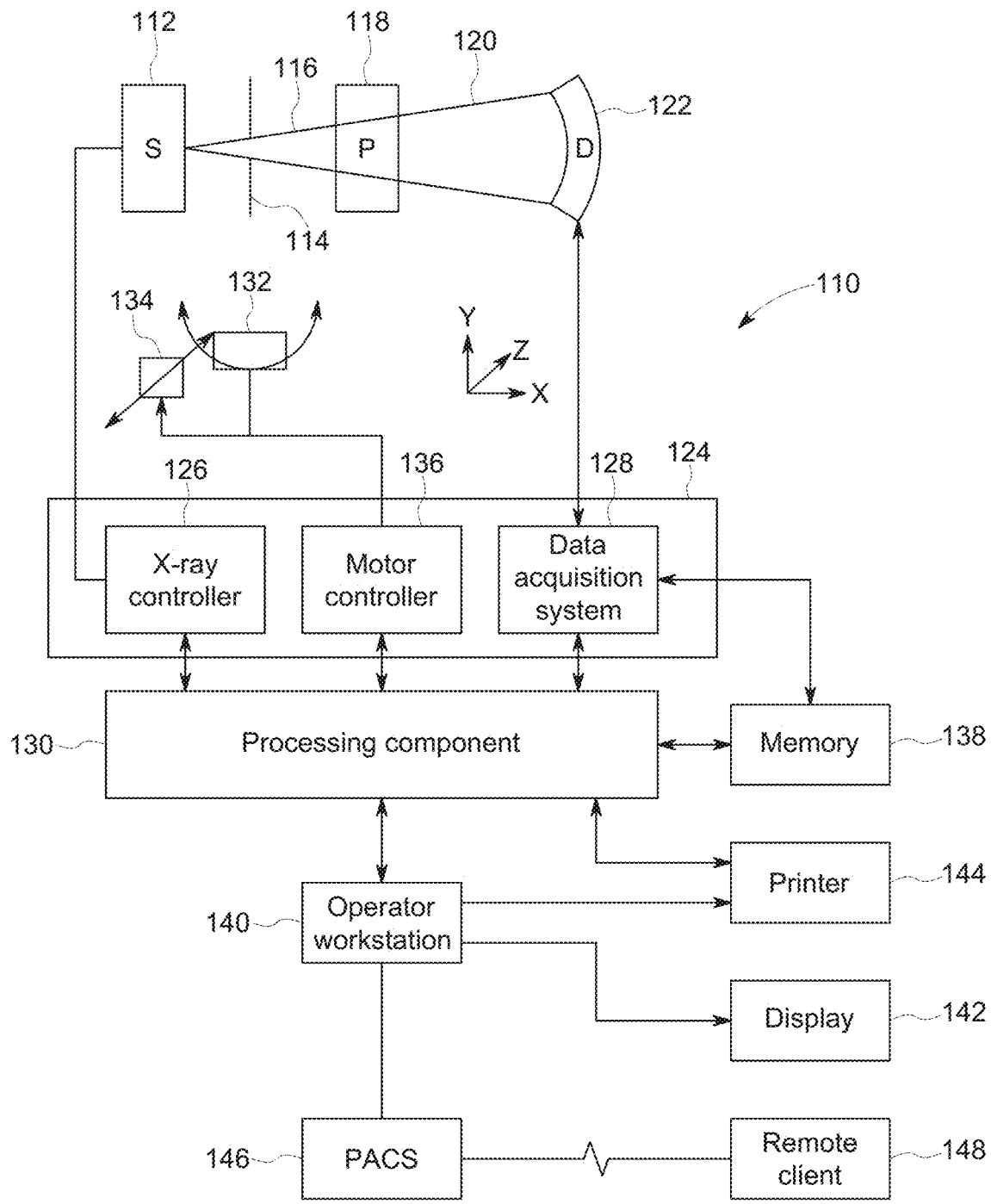
FIG. 2 is a block diagram depicting components of a computed tomography (CT) imaging system, in accordance with aspects of the present disclosure.

With this in mind, an example of an imaging system 110 (i.e., a scanner) is depicted in FIG. 2. In the depicted example, the imaging system 110 is a CT imaging system designed to acquire scan data (e.g., X-ray attenuation data) at a variety of views around a patient (or other subject or object of interest) and suitable for performing image reconstruction using tomographic reconstruction techniques. In the embodiment illustrated in FIG. 2, imaging system 110 includes a source of X-ray radiation 112 positioned adjacent to a collimator 114. The X-ray source 112 may be an X-ray tube, a distributed X-ray source (such as a solid-state or thermionic X-ray source) or any other source of X-ray radiation suitable for the acquisition of medical or other images. In the case of Mill, the measurements are samples in Fourier space (k-space) and can either be applied directly as the input to the neural network or can first be converted to a suitable form.

In the depicted CT example, the collimator 114 shapes or limits a beam of X-rays 116 that passes into a region in which a patient/object 118, is positioned. In the depicted example, the X-rays 116 are collimated to be a cone-shaped beam, i.e., a cone-beam, that passes through the imaged volume. A portion of the X-ray radiation 120 passes through or around the patient/object 118 (or other subject of interest) and impacts a detector array, represented generally at reference numeral 122. Detector elements of the array produce electrical signals that represent the intensity of the incident X-rays 120. These signals are acquired and processed to represent projection or sinogram data from which images of the features within the patient/object 118 are reconstructed.

Source 112 is controlled by a system controller 124, which furnishes both power, and control signals for CT examination sequences, including acquisition of two-dimensional localizer or scout images used to identify anatomy of interest within the patient/object for subsequent scan protocols. In the depicted embodiment, the system controller 124 controls the source 112 via an X-ray controller 126 which may be a component of the system controller 124. In such an embodiment, the X-ray controller 126 may be configured to provide power and timing signals to the X-ray source 112.

Moreover, the detector 122 is coupled to the system controller 124, which controls acquisition of the signals generated in the detector 122. In the depicted embodiment, the system controller 124 acquires the signals generated by the detector using a data acquisition system 128. The data acquisition system 128 receives data collected by readout electronics of the detector 122. The data acquisition system 128 may receive sampled analog signals from the detector 122 and convert the data to digital signals for subsequent processing by a processor 130 discussed below. Alternatively, in other embodiments the digital-to-analog conversion may be performed by circuitry provided on the detector 122 itself. The system controller 124 may also execute various signal processing and filtration functions with regard to the acquired detector signals, such as for initial adjustment of dynamic ranges, interleaving of digital detector data, and so forth.

In the embodiment illustrated in FIG. 2, system controller 124 is coupled to a rotational subsystem 132 and a linear positioning subsystem 134. The rotational subsystem 132 enables the X-ray source 112, collimator 114 and the detector 122 to be rotated one or multiple turns around the patient/object 118, such as rotated primarily in an x,y-plane about the patient. It should be noted that the rotational subsystem 132 might include a gantry or C-arm upon which the respective X-ray emission and detection components are disposed. Thus, in such an embodiment, the system controller 124 may be utilized to operate the gantry or C-arm.

The linear positioning subsystem 134 may enable the patient/object 118, or more specifically a table supporting the patient, to be displaced within the bore of the CT system 110, such as in the z-direction relative to rotation of the gantry. Thus, the table may be linearly moved (in a continuous or step-wise fashion) within the gantry to generate images of particular areas of the patient 118. In the depicted embodiment, the system controller 124 controls the movement of the rotational subsystem 132 and/or the linear positioning subsystem 134 via a motor controller 136.

In general, system controller 124 commands operation of the imaging system 110 (such as via the operation of the source 112, detector 122, and positioning systems described above) to execute examination protocols and to process acquired data. For example, the system controller 124, via the systems and controllers noted above, may rotate a gantry supporting the source 112 and detector 122 about a subject of interest so that X-ray attenuation data may be obtained at one or more views relative to the subject. In the present context, system controller 124 may also include signal processing circuitry, associated memory circuitry for storing programs and routines executed by the computer (such as routines for estimating motion using the techniques described herein), as well as configuration parameters, image data, and so forth.

In the depicted embodiment, the detector signals acquired and processed by the system controller 124 are provided to a processing component 130 for estimation of motion state (or phase), bolus parameter, or timing of the diagnostic scan, in accordance with the presently disclosed algorithms. The raw data acquired during the diagnostic scan can be reconstructed into diagnostic images using a reconstruction algorithm known in the art, such as FBP (filtered back-projection), MBIR (model-based iterative reconstruction), etc. The processing component 130 may be one or more general or application-specific microprocessors. The data collected by the data acquisition system 128 may be transmitted to the processing component 130 directly or after storage in a memory 138. Any type of memory suitable for storing data might be utilized by such an exemplary system 110. For example, the memory 138 may include one or more optical, magnetic, and/or solid state memory storage structures. Moreover, the memory 138 may be located at the acquisition system site and/or may include remote storage devices for storing data, processing parameters, and/or routines for motion state estimation, or scan timing estimation, as described below.

The processing component 130 may be configured to receive commands and scanning parameters from an operator via an operator workstation 140, typically equipped with a keyboard and/or other input devices. An operator may control the system 110 via the operator workstation 140. Thus, the operator may observe the reconstructed images and/or otherwise operate the system 110 using the operator workstation 140. For example, a display 142 coupled to the operator workstation 140 may be utilized to observe the reconstructed images and to control imaging. Additionally, the images may also be printed by a printer 144 which may be coupled to the operator workstation 140.

Further, the processing component 130 and operator workstation 140 may be coupled to other output devices, which may include standard or special purpose computer monitors and associated processing circuitry. One or more operator workstations 140 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 140 may also be coupled to a picture archiving and communications system (PACS) 146. PACS 146 may in turn be coupled to a remote client 148, radiology department information system (RIS), hospital information system (HIS) or to an internal or external network, so that others at different locations may gain access to the raw or processed image data.

While the preceding discussion has treated the various exemplary components of the imaging system 110 separately, these various components may be provided within a common platform or in interconnected platforms. For example, the processing component 130, memory 138, and operator workstation 140 may be provided collectively as a general or special purpose computer or workstation configured to operate in accordance with the aspects of the present disclosure. In such embodiments, the general or special purpose computer may be provided as a separate component with respect to the data acquisition components of the system 110 or may be provided in a common platform with such components. Likewise, the system controller 124 may be provided as part of such a computer or workstation or as part of a separate system dedicated to image acquisition.

With this background and context discussion in mind, the present disclosure relates to determining an optimal scan timing for imaging of non-static objects (e.g., cardiac imaging) undergoing periodic or nearly periodic motion in the second to sub-second time frame by analyzing raw data for estimating cardiac and/or respiratory motion states. In one implementation, the raw data is analyzed to evaluate and determine an optimal scan timing based on bolus parameters (e.g., peak opacification, scan timing for optimal imaging of the uptake and/or washout phase of the contrast agent, etc). To the extent that the present examples are in the context of CT scanning, the term "raw data", as used in the CT context, corresponds to sinogram (or projection) data. However, as may be appreciated, the present technique may also be applied in the context of other scanner types, such as MM, where the raw data may be k-space data.

As noted above, scan timing may be based on one or more of contrast agent opacification level, cardiac phase, or respiratory phase. Thus, in CT, scan timing may be determined by monitoring some or all of 'cardiac phase', 'bolus parameter', and 'respiratory phase'. Cardiac phase indicates cardiac cycle stage such as end-diastole or end-systole of heart, and is conventionally enabled by using an electrocardiogram (ECG) device. Bolus level is the contrast agent concentration level in the target vessel or organ after injection, and it is typically measured by tracking the image voxel values of the target area (or a suitable anatomical area nearby) in reconstructed images. Conventionally, respiratory phase may be measured using a patient-worn device or other means.

In contrast to these conventional techniques, in accordance with the present disclosure one or more of the cardiac phase, bolus parameter(s), and respiratory phase are measured by real-time, sinogram-based (i.e., raw or un-reconstructed scan data) cardiac phase monitoring, bolus parameter monitoring, and/or respiratory phase monitoring. As used herein, bolus parameters may correspond to an opacity or contrast concentration, a travel time or flow rate or change in opacity over time, and so forth. Examples of bolus parameters, as used herein, include but are not limited to: 1) a relative intensity of the contrast (relative to the peak contrast); 2) an absolute HU intensity level of the contrast; 3) a time offset relative to the time of peak contrast; 4) a binary value where 1 means the scan should be triggered immediately; or 5) a "phase", where 0 means, for example, that the contrast is just starting to come in, 0.5, for example, indicates peak contrast is occurring, and 1 means that the contrast has dropped below some fraction of the peak contrast.

In the context of perfusion imaging (e.g., for applications to cardiac, liver, head, etc.), for example, the uptake (arterial phase) and washout (venous phase) of the contrast agent in the region/organ of interest are of particular interest. In this context the focus of the present technique is on creating optimal timing information for acquisition of (diagnostic) scan data based on the temporal evolution of the bolus (contrast agent concentration) as well as temporal progression of the bolus through different parts of the imaged anatomy. In one instance there may be only little motion present (cardiac motion or respiratory motion) and the analysis of the raw scan data is more targeted towards estimating bolus parameters and estimating optimal scan timing. This scan timing information may comprise timing information for two or more diagnostic acquisitions (e.g., acquisitions for an arterial phase which is followed by an acquisition for a venous phase, where timing information for both acquisitions is generated by the analysis of the raw scan data acquired during the monitoring phase). In another embodiment, after triggering a diagnostic scan phase based on the analysis of the raw scan data acquired during an initial monitoring phase, the system transitions back into a monitoring stage during which data is again acquired for analysis towards estimating the timing of a subsequent diagnostic scan stage. In the context of perfusion imaging, the uptake/washout time for a contrast bolus may take 30-60 seconds or more.

In one embodiment the timing of the diagnostic scan may be estimated directly based on the raw un-reconstructed scan data acquired during a monitoring stage and may be estimated concurrent with the acquisition during the monitoring stage. As discussed herein, the present techniques may be based on or performed solely on raw scan data (e.g., raw CT data or sinogram data). In one implementation, CT sinogram data obtained during a monitoring phase used to collect the data for monitoring one or more of the above phases may be relatively sparse (e.g., the acquired data during the monitoring stage may consist of projection data for a sparse set of view angles—as opposed to the diagnostic scan data which is continuously acquired for densely sampled view angles for a certain angular range) and low-dose. These methods allow accurate scan timing to be found without the use of ECG equipment, without use of an additional timing bolus, and without use of a respiratory measuring device, and with minimal computational or other delays.

Figure 3:
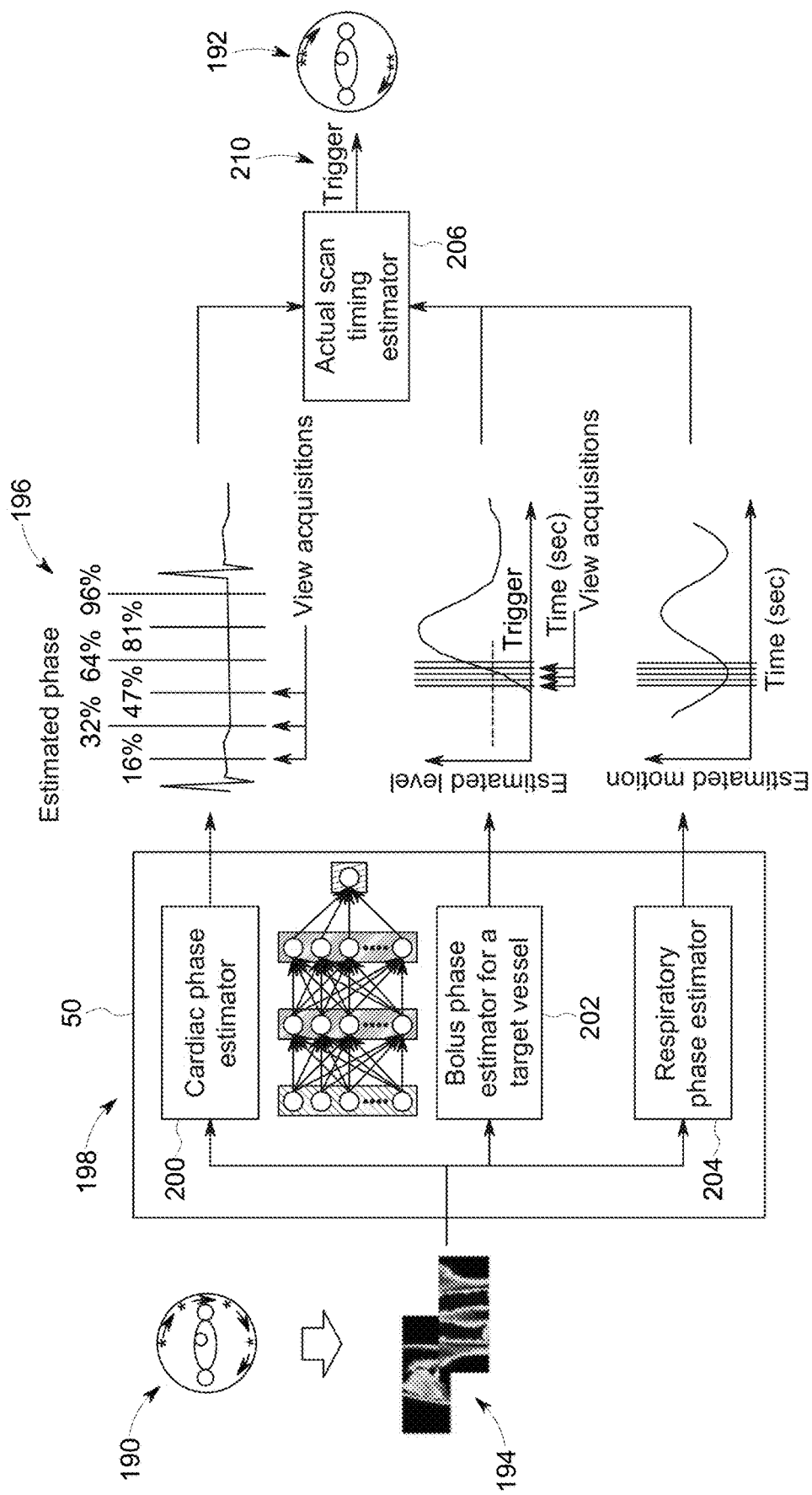
FIG. 3 depicts a process flow for determining diagnostic scan timing, in accordance with aspects of the present disclosure.

Turning to the figures, FIG. 3 depicts an overview of the present technique in a CT context. As shown, the patient may undergo a low-dose monitoring scan stage 190 initially. As used herein, a monitoring scan 190 is distinct from a diagnostic scan 192 in that the acquired scan data is acquired at an X-ray dose not suitable for reconstruction into a diagnostic quality image. By way of example, the monitoring scan 190 may be performed by pulsing the X-ray tube, resulting in a sparse-view dataset (sinogram) 194, corresponding to lower radiation dose. Conversely, the diagnostic scan 192 may be performed in a continuous manner and at a full X-ray dose. With these distinction between the monitoring scan 190 and diagnostic scan 192 in mind, in one embodiment the imaging system is a CT scanner with large volumetric coverage, i.e., sufficiently large to cover the entire heart or brain, such as 14 cm to 16 cm. With this type of scanner, the patient can remain in the same position and the collimation can remain unchanged for the monitoring scan 190 relative to the diagnostic scan 192 and the time delay is minimized between the two scan stages. Projection data 194, as used herein, may consist of one or more projection images. In one embodiment, projection data consists of projection data acquired in the AP (anterior-posterior) position. i.e., the X-ray source and detector are in an angular position such as to acquire an AP view of the patient. In one embodiment, one or more AP views (or sets of projections in small angular intervals around the AP position) are acquired. In another embodiment, AP views are collected as well as views at other angular directions. Other angular sampling strategies may be used as well, including dense sampling, random sampling, and so forth. This data may be acquired while the gantry is continuously rotating and the X-ray tube is pulsed during the monitoring phase.

Projection data (e.g., sinogram 194) acquired during the monitoring scan 190 may be subjected to sinogram analysis 198 to determine timing as to when to start the diagnostic scan 192. In the depicted example, the sinogram analysis 198 is performed to estimate one or more of a cardiac phase, a bolus parameter, and/or a respiratory phase. For example, in one embodiment, sinogram analysis 198 may be performed using one or more neural networks 50 trained to (in combination or alone) perform one or more of cardiac phase estimation 200, bolus parameter estimation 202, and/or respiratory phase estimation 204. In other embodiments, other parameters may also be estimated, such as blood flow, contrast flow speed, flow path, and so forth. In yet another embodiment, diagnostic scan timing may be directly estimated through sinogram analysis 198. In one embodiment the projection data may be pre-processed, e.g., to identify anatomical regions of interest. The output of the pre-processing can then be used as an (additional) input to the sinogram analysis 198 or to crop the data that is used as an input.

In accordance with present embodiments, the cardiac phase estimation 200 determines the quiescent phase of the heart cycle. The cardiac phase may be estimated in various ways. In a phase based approach, the cardiac phase is determined relative to the ECG R-R interval (i.e., peak to peak interval) for each view acquisition (shown as the output of phase estimation 200 of FIG. 3). This can be done as a % of the R-R interval or using a fixed delay after the R-peak. It is generally accepted that the least cardiac motion occurs during the diastole stage (50%-60%), therefore this interval can be used to predict the optimal acquisition timing in a future heartbeat. In one embodiment estimating the cardiac phase comprises directly estimating the timing of a quiescent cardiac phase, which is then used for triggering the acquisition of the diagnostic scan data.

Alternatively, cardiac phase can be estimated using a motion based approach. In a motion based approach, the heart motion level is directly estimated from the raw data. A scan time or a range of view angles are then identified that are expected to contain the least motion during a future heart-beat. Acquisition timing can then be determined based upon this estimation.

Bolus parameter estimation 202 may be used to determine when the peak (or a desired level) of contrast concentration (e.g., opacity) will occur or other relevant bolus characteristics, as discussed herein. For each projection view angle (or from a set a projections), the bolus level or parameter is estimated. From a series of bolus parameters (e.g., levels or concentrations) as a function of time (shown as the output of the bolus parameter estimation 202), a suitable scan time can be estimated by evaluating when the contrast level exceeds a pre-defined threshold or by curve fitting of a typical bolus shape, for instance. In general, an algorithm may be used to determine when the bolus opacification is at a good level to start the diagnostic scan 192. In most cases, a higher bolus opacification is better than a lower one, but other considerations of the timing may also be considered. For example, it may be preferred to scan a second or two before the peak to ensure that there is little contrast in the cardiac veins. Once the condition is met (and typically also the cardiac phase condition is met), the diagnostic scan 192 can be triggered, i.e., the X-ray tube start to emit continuously or at a higher technique or dose.

The respiratory phase estimation 204 finds respiratory motion level (shown as an output of respiratory phase estimation 204) of a patient. Once motion level is minimum or small enough, and other conditions are met with respect to cardiac phase and bolus parameter(s), the diagnostic scan 192 may be triggered.

In practice, the estimated results 196 of the various estimators may be numeric values and may be separate numeric estimations for each motion-related parameter (e.g., cardiac phase, respiratory phase, bolus parameter(s)) being evaluated or may be a combined or aggregate motion indicator or number generally indicative of motion from the various monitored sources e.g., a generic motion number or indicator for the region of interest. In the depicted example, the estimates 196 may be inputs to a timing estimator 206 that is configured to output a trigger 210 or other timing signal that can cause the diagnostic scan 192 to be performed. Depending on the implementation, the timing estimator 206 may be an algorithm implemented on a general or application-specific processor that encodes a routine that evaluates the estimated results 196 to generate the trigger 210. In other implementations, the timing estimator 206 may be a neural network 50, as discussed herein, that is trained to receive an input of the estimated results 196 and output the trigger 210 when appropriate.

The various estimated results 196 may be generated by separate, individually trained networks, or by a combined network that generates multiple outputs. Similarly, the various processing steps may be combined into a single larger network that directly generates the trigger 210. In such a configuration, smaller sub-networks may be pre-trained such as to generate various estimates 196, and the pre-trained networks may then be used to initialize the training of the larger network. In one embodiment, the optimal scan timing is determined based on image quality metrics extracted from reconstructed image data. i.e., the optimal timing is determined to be the time instant when the resulting reconstructed images show a suitable amount of motion blurring (e.g., minimal blurring), the maximum (or most consistent) contrast of opacified vessels, and so forth. This image quality evaluation may be performed manually, or by using appropriate processing steps (which may also utilize deep learning). While this involves the step of image reconstruction in generating appropriate training data, the use of the resulting trained network does not utilize an image reconstruction step, and therefore has the advantageous properties as discussed herein above.

As noted above, sinogram analysis 198 may be performed using one or more trained neural networks 50 (i.e., deep learning or machine learning) to estimate one or more of cardiac phase, bolus parameter(s), or respiratory phase. The neural network(s) 50 may be trained offline to receive a single projection or a set of projections (e.g., sinograms 194) generated using a monitoring scan 190 and to output one or more of the estimated phases and parameters of interest or, in one embodiment, the actual scan time or trigger signal 210 for the diagnostic scan 192.

Figure 4:
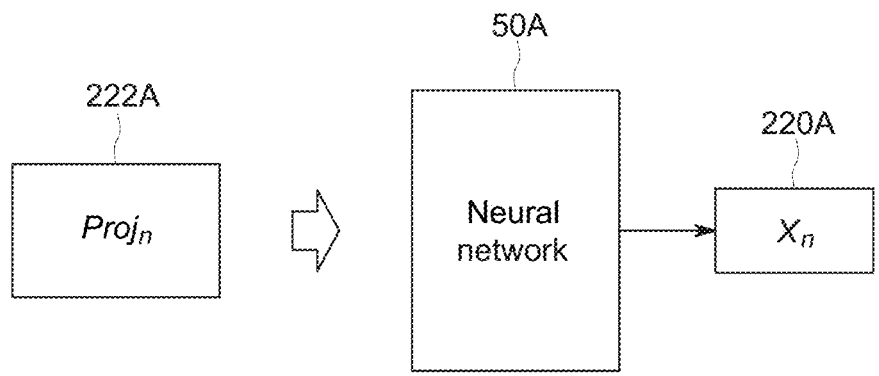
FIG. 4 depicts an example of a suitable neural network implementation, in accordance with aspects of the present disclosure.
Figure 5:
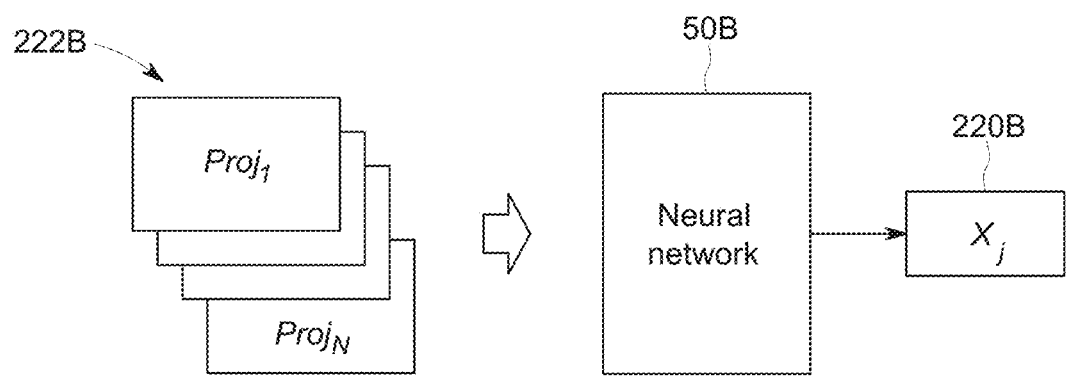
FIG. 5 depicts an example of a further suitable neural network implementation, in accordance with aspects of the present disclosure.
Figure 6:
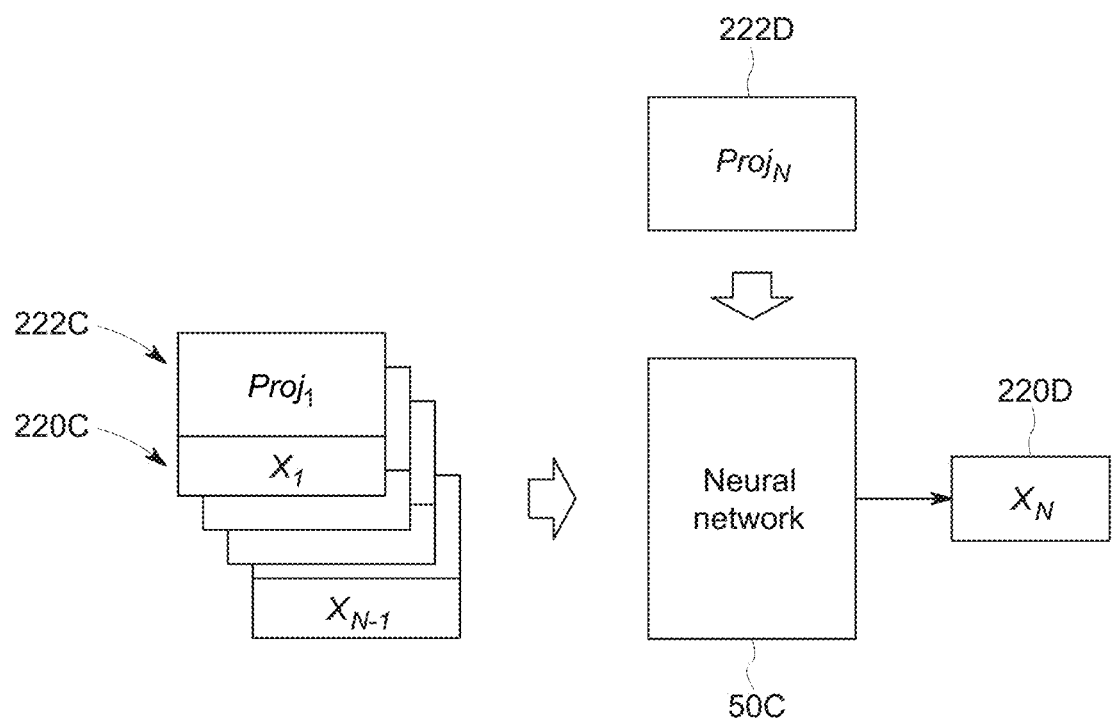
FIG. 6 depicts an example of another suitable neural network implementation, in accordance with aspects of the present disclosure.

Turning to FIGS. 4-6, three examples of neural networks 50 are illustrated that are suitable for use in the present technique. As used herein, the term projn represents the projection data 194 at time n, and the term $x_n$ represents the estimated value (or a vector containing a set of values) 220, such as cardiac phase, motion level, or bolus opacification level at time n. A set of two values may be preferred to a single value when representing cardiac phase, for example, due to the periodicity of the phase (a phase of 1 and a phase of 0 are actually the same). For example, the network may output the cosine of the phase times two pi and the sine of the phase times 2 pi rather than the phase itself.

With this in mind, FIG. 4 depicts an implementation in which the trained neural network 50A receives a single projection 222A as an input at time n and outputs a number $x_n$ representing the estimate 220A at time n. As used in the present examples shown in FIGS. 4-6, the estimate 220 may be, as described above, an estimate of a cardiac phase, a bolus parameter, a respiratory phase or a more generalized motion quantification derived based on one or more of the cardiac or respiratory motion and/or opacity. Indeed, in some implementations the estimate 220, depending on the training of the neural network 50, may itself be the trigger indicator 210 used to determine when to start the diagnostic scan 192.

Turning to FIG. 5, a second implementation is depicted in which the trained neural network 50B receives a series of projections 222B (e.g., projections acquired at times 1, 2, . . . N) as inputs and outputs a number $x_j$ representing the estimate 222B at one time 1, 2, . . . or N. Thus, in this implementation the neural network 50B generates the estimate 220B from a moving window of projections 222B which may be a set of past projection data or, optionally, may include future projection data (i.e., the estimate may be centered in time with respect to the moving window).

Turning to FIG. 6, a third implementation is depicted in which the trained neural network 50C receives as inputs both: (a) a current projection 222D and (b) a series of prior projections 222C with associated estimates 220C. The trained neural network 50C provides as an output a number $x_N$ representing the estimate 220D at time N.

With the preceding examples in mind, the implementations of FIGS. 5 and 6 may be useful for capturing dynamic information using time-series data since cardiac phase and contrast opacification changes over time. With this in mind, neural networks 50 employed in this manner can be implemented as recurrent neural network having feedback loops.

As may be appreciated from the preceding discussion and examples, the present cardiac phase monitoring and bolus tracking works using only raw, i.e., unreconstructed, scan data, such as CT sinograms, and can therefore eliminate the need to apply an ECG device and/or respiratory monitor to patients. This can decrease patient stress and reduce operator burden. Further, the present techniques can eliminate the need for a separate timing bolus and associated scans and therefore save time, contrast dose, and radiation dose. The above advantages can improve clinical workflow for cardiac CT, but can be expanded to other types of CT scans as well as MR scans.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of estimating an optimal scan timing for a diagnostic image acquisition scan of a non-static object, comprising the steps of:
    performing a monitoring scan using scan parameters different than those used in the diagnostic image acquisition scan, wherein the monitoring scan generates unreconstructed scan data;
    as the monitoring scan is being performed, estimating an object motion phase of the non-static object based on the unreconstructed scan data;
    as the monitoring scan is being performed, determining a diagnostic scan trigger based on at least a current object motion phase; and
    performing the diagnostic image acquisition scan based on the diagnostic scan trigger such that the diagnostic image acquisition occur in substantially real-time relative to the determination of the diagnostic scan trigger.

2. The method of claim 1, wherein estimating the object motion phase comprises providing the unreconstructed scan data to one or more machine learning models trained to receive the unreconstructed scan data and to estimate at least one of the object motion phase or the diagnostic scan trigger based on the unreconstructed scan data.

3. The method of claim 2, wherein the one or more machine learning models comprise at least one neural network configured to receive a projection corresponding to a time n as input and to output an estimate of a cardiac phase, a bolus parameter, a respiratory phase, or an aggregate motion measure at the time n.

4. The method of claim 2, wherein the one or more machine learning models comprise at least one neural network configured to receive a set of projections acquired over a time range as input and to output an estimate of a cardiac phase, a bolus parameter, a respiratory phase, or an aggregate motion measure at any time point based on the set of projections.

5. The method of claim 2, wherein the one or more machine learning models comprise at least one neural network configured to output an estimate of a cardiac phase, a bolus parameter, a respiratory phase, or an aggregate motion measure at a time n based on an input of:
    a set of projections acquired at different times of a time range prior to n;
    the estimate of cardiac phase, bolus parameter, respiratory phase, or aggregate motion measure determined for each projection of the set of projections; and
    a projection corresponding to the time n.

6. The method of claim 1, wherein the object motion phase comprises one or more of a cardiac phase, a respiratory phase, or an aggregate motion measure.

7. The method of claim 1, wherein the diagnostic scan trigger is determined based on a bolus timing in addition to the object motion phase of the non-static object.

8. The method of claim 1, wherein the monitoring scan comprises a computed tomography (CT) scan in which an X-ray tube is pulsed so as to generate a sparse-view projection dataset corresponding to a lower X-ray dose relative to that delivered during the diagnostic scan.

9. An imaging system comprising:
    a memory encoding processor-executable routines;
    a processing component configured to access the memory and execute the processor-executable routines, wherein the routines, when executed by the processing component, cause the processing component to:
        perform a monitoring scan using scan parameters different than those used in a diagnostic image acquisition scan, wherein the monitoring scan generates unreconstructed scan data;
        estimate an object motion phase of a non-static object as the monitoring scan is being performed and based on the unreconstructed scan data;
        determine a diagnostic scan trigger as the monitoring scan is being performed and based on at least a current object motion phase; and
        perform the diagnostic image acquisition scan based on the diagnostic scan trigger such that the diagnostic image acquisition occur in substantially real-time relative to the determination of the diagnostic scan trigger.

10. The imaging system of claim 9, wherein the imaging system comprises one of a computed tomography imaging system or a magnetic resonance imaging system.

11. The imaging system of claim 9, wherein the monitoring scan comprises a scan in which an X-ray tube is pulsed so as to generate a sparse-view projection dataset corresponding to a lower X-ray dose relative to that delivered during the diagnostic scan.

12. The imaging system of claim 9, wherein the object motion phase is estimated by one or more machine learning models trained to receive the unreconstructed scan data and to estimate at least one of the object motion phase or the diagnostic scan trigger based on the unreconstructed scan data.

13. The imaging system of claim 12, wherein the one or more machine learning models comprise at least one neural network configured to receive a projection corresponding to a time n as input and to output the estimate of cardiac phase, bolus parameter, respiratory phase, or aggregate motion measure at the time n.

14. The imaging system of claim 12, wherein the one or more machine learning models comprise at least one neural network configured to receive a set of projections acquired over a time range as input and to output an estimate of a cardiac phase, a bolus parameter, a respiratory phase, or an aggregate motion measure at any time point based on the set of projections.

15. The imaging system of claim 12, wherein the one or more machine learning models comprise at least one neural network configured to output an estimate of a cardiac phase, a bolus parameter, a respiratory phase, or an aggregate motion measure at a time n based on an input of:
    a set of projections acquired at different times of a time range prior to n;

the estimate of cardiac phase, bolus parameter, respiratory phase, or aggregate motion measure determined for each projection of the set of projections; and a projection corresponding to the time n.

16. A non-transitory machine-readable storage medium storing executable instructions that, when executed by a processor, cause operations to be performed comprising:

performing a monitoring scan using scan parameters different than those used in a diagnostic image acquisition scan, wherein the monitoring scan generates unreconstructed scan data;

estimating an object motion phase of a non-static object as the monitoring scan is being performed and based on the unreconstructed scan data;

determining a diagnostic scan trigger as the monitoring scan is being performed and based on at least a current object motion phase; and performing the diagnostic image acquisition scan based on the diagnostic scan trigger such that the diagnostic image acquisition occur in substantially real-time relative to the determination of the diagnostic scan trigger.

17. The non-transitory machine-readable storage medium of claim 16, wherein estimating the object motion phase comprises providing the unreconstructed scan data to one or more machine learning models trained to receive the unreconstructed scan data and to estimate at least one of the object motion phase or the diagnostic scan trigger based on the unreconstructed scan data.

18. The non-transitory machine-readable storage medium of claim 16, wherein the one or more machine learning models comprise at least one neural network configured to receive a projection corresponding to a time n as input and to output the estimate of cardiac phase, bolus parameter, respiratory phase, or aggregate motion measure at the time n.

19. The non-transitory machine-readable storage medium of claim 16, wherein the one or more machine learning models comprise at least one neural network configured to receive a set of projections acquired over a time range as input and to output an estimate of a cardiac phase, a bolus parameter, a respiratory phase, or an aggregate motion measure based on the set of projections.

20. The non-transitory machine-readable storage medium of claim 16, wherein the one or more machine learning models comprise at least one neural network configured to output an estimate of a cardiac phase, a bolus parameter, a respiratory phase, or an aggregate motion measure at a time n based on an input of:

a set of projections acquired at different times of a time range prior to n;

the estimate of cardiac phase, bolus parameter, respiratory phase, or aggregate motion measure determined for each projection of the set of projections; and a projection corresponding to the time n.

* * * * *